US010485519B2

United States Patent
Imamura

(10) Patent No.: US 10,485,519 B2
(45) Date of Patent: Nov. 26, 2019

(54) ULTRASONIC DIAGNOSTIC APPARATUS, BIOLOGICAL SIGNAL ACQUISITION APPARATUS AND METHOD FOR CONTROLLING ULTRASONIC DIAGNOSTIC APPARATUS

(71) Applicant: Toshiba Medical Systems Corporation, Otawara-shi (JP)

(72) Inventor: Tomohisa Imamura, Nasushiobara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 1019 days.

(21) Appl. No.: 14/577,061

(22) Filed: Dec. 19, 2014

(65) Prior Publication Data

US 2015/0105664 A1 Apr. 16, 2015

Related U.S. Application Data

(63) Continuation of application No. PCT/JP2013/067949, filed on Jul. 1, 2013.

(30) Foreign Application Priority Data

Jul. 2, 2012 (JP) ................................ 2012-148115

(51) Int. Cl.
*A61B 8/00* (2006.01)
*A61B 5/00* (2006.01)
(Continued)

(52) U.S. Cl.
CPC ............ *A61B 8/543* (2013.01); *A61B 5/0006* (2013.01); *A61B 5/0402* (2013.01);
(Continued)

(58) Field of Classification Search
CPC .... A61B 8/54; A61B 8/44; A61B 8/14; A61B 8/543; A61B 8/56; A61B 5/0006; A61B 5/0402; A61B 5/743; A61B 5/0408
See application file for complete search history.

(56) References Cited

U.S. PATENT DOCUMENTS 7,130,190 B1 * 10/2006 Baker .................. G06F 1/1632
361/695
7,450,746 B2 11/2008 Yang et al.
(Continued)

FOREIGN PATENT DOCUMENTS

CN 101524282 A 9/2009
JP H09-038048 A1 2/1997
(Continued)

OTHER PUBLICATIONS

Office Action dated Dec. 16, 2015 in Chinese Patent Application No. 201380001252.X.
(Continued)

*Primary Examiner* — Bo Joseph Peng
(74) *Attorney, Agent, or Firm* — Oblon, McClelland, Maier & Neustadt, L.L.P.

(57) ABSTRACT

According to one embodiment, an ultrasonic diagnostic apparatus includes an imaging system, a biological signal receiving system and a biological signal acquisition apparatus. The imaging system is configured to acquire ultrasonic image data by transmitting and receiving an ultrasonic wave to and from an object. The biological signal receiving system is configured to wirelessly transmit a transmission request of a biological signal of the object, receive the biological signal of the object wirelessly transmitted as a response to the transmission request, and output the received biological signal to an output unit. The transmission request is transmitted to a biological signal acquisition apparatus. The biological signal acquisition apparatus control system is
(Continued)

configured to wirelessly transmit information according to an operating condition of at least one of the imaging system and the biological signal receiving system. The information is transmitted to the biological signal acquisition apparatus.

10 Claims, 3 Drawing Sheets

(51) Int. Cl.
 *A61B 5/0402* (2006.01)
 *A61B 5/0408* (2006.01)
 *A61B 8/14* (2006.01)
(52) U.S. Cl.
 CPC ............ *A61B 5/0408* (2013.01); *A61B 5/743* (2013.01); *A61B 8/44* (2013.01); *A61B 8/54* (2013.01); *A61B 8/56* (2013.01); *A61B 8/14* (2013.01)

(56) References Cited

U.S. PATENT DOCUMENTS

| | | | | |
|---|---|---|---|---|
| 7,805,263 B2* | 9/2010 | Mack | ................... | A61N 1/3708 320/132 |
| 2008/0101532 A1* | 5/2008 | Tkaczyk | ................ | A61B 6/541 378/8 |
| 2008/0285819 A1* | 11/2008 | Konofagou | .............. | A61B 8/08 382/128 |
| 2009/0005679 A1* | 1/2009 | Dala-Krishna | ...... | A61B 8/0883 600/437 |
| 2009/0069642 A1* | 3/2009 | Gao | ................... | A61B 5/02055 600/300 |
| 2009/0224611 A1 | 9/2009 | Chen | | |

FOREIGN PATENT DOCUMENTS

| | | | |
|---|---|---|---|
| JP | 2006-212161 | A1 | 8/2006 |
| JP | 2007-061431 | A1 | 3/2007 |
| JP | 2008-113799 | A1 | 5/2008 |
| JP | 2008-518711 | A1 | 6/2008 |
| JP | 2009-502354 | A1 | 1/2009 |
| JP | 2009-189570 | A1 | 8/2009 |
| JP | 2009-213868 | A1 | 9/2009 |
| JP | 2010-119587 | A1 | 6/2010 |
| JP | 2012-085893 | A1 | 5/2012 |

OTHER PUBLICATIONS

Office Action dated May 16, 2017 in Japanese Patent Application No. 2013-138316.
Combined Chinese Office Action and Search Report dated Feb. 26, 2015 in Patent Application No. 201380001252.X (with English Translation of Category of Cited Documents).
International Preliminary Report on Patentability and Written Opinion dated Jan. 15, 2015 in PCT/JP2013/067949 (submitting English translation only).
International Search Report dated Aug. 27, 2013 for PCT/JP2013/067949 filed on Jul. 1, 2013 with English Translation.
Written Opinion dated Aug. 27, 2013 for PCT/JP2013/067949 filed on Jul. 1, 2013.

* cited by examiner

ULTRASONIC DIAGNOSTIC APPARATUS, BIOLOGICAL SIGNAL ACQUISITION APPARATUS AND METHOD FOR CONTROLLING ULTRASONIC DIAGNOSTIC APPARATUS

CROSS REFERENCES TO RELATED APPLICATIONS

This is a continuation of Application PCT/JP2013/67949, filed Jul. 1, 2013.

This application is based upon and claims the benefit of priority from Japanese Patent Application No. 2012-148115, filed Jul. 2, 2012; the entire contents of which are incorporated herein by reference.

FIELD

Embodiments described herein relate generally to an ultrasonic diagnostic apparatus, a biological signal acquisition apparatus and a method for controlling an ultrasonic diagnostic apparatus.

BACKGROUND

Conventionally, in a diagnosis using an ultrasonic diagnostic apparatus, an ECG (electro cardiogram) is often referred. In order to refer an ECG signal, multiple ECG sensors are attached to positions, such as breast parts, of an object. Then, an ECG signal acquired with each ECG sensor is output to a signal processing system via signal lines. The ECG waveform generated in the signal processing system of the ECG signals is displayed on a monitor installed near the ultrasonic diagnostic apparatus. Thereby, a user becomes possible to perform an ultrasonic diagnosis with referring to the ECG waveform.

Moreover, the acquired ECG signal can also be referred to in signal processing for generation and display of ultrasonic diagnosis image data.

PRIOR TECHNICAL LITERATURE

[Patent literature 1] JPA 2012-85893

However, it is necessary to attach three cables for ECG signals to the breast and the legs of an object in order to display the ECG waveform of the object. Moreover, during an examination using an ultrasonic diagnostic apparatus, a cable for an ECG signal sometimes slips and falls by a motion of the object. In that case, the cable for the ECG signal is attached to the object again.

For this reason, in order to acquire ECG signals in an ultrasonic diagnosis, very complicated work occurs. In addition, in a case of attaching a cable for an ECG signal repeatedly, it is important to give a care to the hygiene.

Especially, an ultrasonic diagnosis and a load by a treadmill are repeated in a stress echo examination. For this reason, the work to attach the cables for ECG signals to an object repeatedly is needed. Furthermore, in a stress echo examination, performing an ultrasonic diagnosis as soon as possible is desired after putting a load on an object. Therefore, a user has to attach the cables for ECG signals to the object in a short time.

Accordingly, an object of the present invention is to provide an ultrasonic diagnostic apparatus, a biological signal acquisition apparatus and a method for controlling an ultrasonic diagnostic apparatus which can acquire an ECG waveform simply by less work.

DETAILED DESCRIPTION

Figure 1:
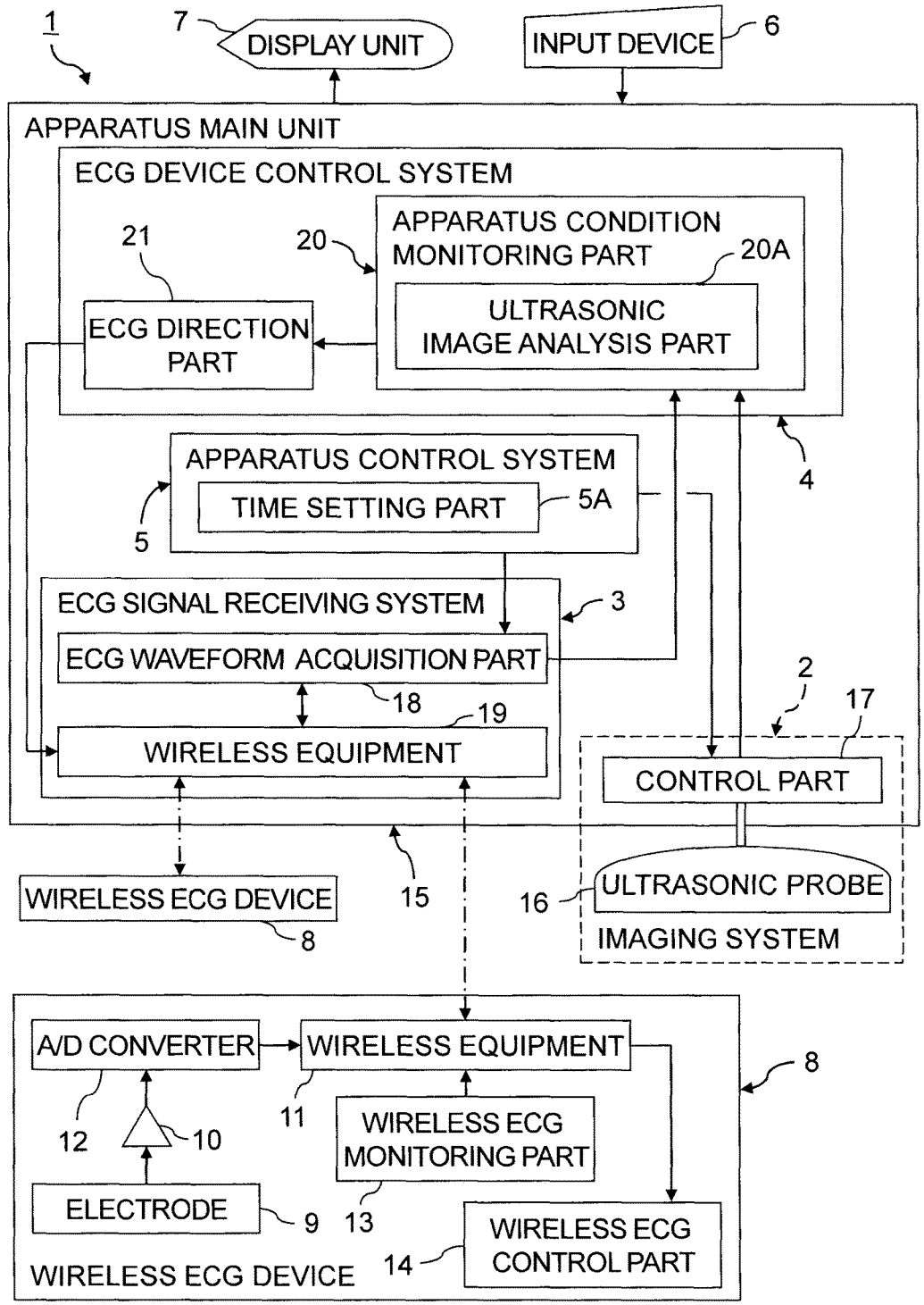
FIG. 1 is a functional block diagram of an ultrasonic diagnostic apparatus according to an embodiment of the present invention.

In general, according to one embodiment, an ultrasonic diagnostic apparatus includes an imaging system, a biological signal receiving system and a biological signal acquisition apparatus. The imaging system is configured to acquire ultrasonic image data by transmitting and receiving an ultrasonic wave to and from an object. The biological signal receiving system is configured to wirelessly transmit a transmission request of a biological signal of the object, receive the biological signal of the object wirelessly transmitted as a response to the transmission request, and output the received biological signal to an output unit. The transmission request is transmitted to a biological signal acquisition apparatus. The biological signal acquisition apparatus control system is configured to wirelessly transmit information corresponding to an operating condition of at least one of the imaging system and the biological signal receiving system. The information is transmitted to the biological signal acquisition apparatus.

Further, according to another embodiment, an ultrasonic diagnostic apparatus includes an imaging system, a biological signal receiving system and an apparatus control system. The imaging system is configured to acquire ultrasonic image data by transmitting and receiving an ultrasonic wave to and from an object. The biological signal receiving system is configured to wirelessly transmit a transmission request of a biological signal of the object, receive the biological signal of the object wirelessly transmitted as a response to the transmission request, and output the received biological signal to an output unit. The transmission request is transmitted to a biological signal acquisition apparatus. The apparatus control system is configured to wirelessly receive information from the biological signal acquisition apparatus and control at least one of the imaging system and the biological signal receiving system corresponding to the information. The information indicates an operating condition of the biological signal acquisition apparatus.

Further, according to another embodiment, a biological signal acquisition apparatus includes a sensor part, a biological signal transmitting part and a control part. The sensor part is configured to acquire a biological signal from an object. The biological signal transmitting part is configured to wirelessly receive a transmission request of the biological signal and wirelessly transmit the biological signal to the ultrasonic diagnostic apparatus as a response to the transmission request. The transmission request is received from an ultrasonic diagnostic apparatus. The control part is configured to wirelessly receive information corresponding to an operating condition of the ultrasonic diagnostic apparatus and control the sensor part according to the information. The information is received from the ultrasonic diagnostic apparatus.

Further, according to another embodiment, a biological signal acquisition apparatus includes a sensor part, a biological signal transmitting part, a control part and an operational information transmitting part. The sensor part is configured to acquire a biological signal from an object. The biological signal transmitting part is configured to wirelessly receive a transmission request of the biological signal and wirelessly transmit the biological signal to the ultrasonic diagnostic apparatus as a response to the transmission request. The transmission request is received from an ultrasonic diagnostic apparatus. The control part is configured to control the sensor part. The operational information transmitting part is configured to transmit information to the ultrasonic diagnostic apparatus. The information indicates an operating condition of at least one of the sensor part, the biological signal transmitting part and the control part.

Further, according to another embodiment, a method for controlling an ultrasonic diagnostic apparatus includes: controlling a biological signal receiving system to wirelessly transmit a transmission request of a biological signal of an object, receive the biological signal of the object wirelessly transmitted as a response to the transmission request, and output the received biological signal to an output unit; and transmitting information wirelessly using the wireless equipment. The transmission request is transmitted to a biological signal acquisition apparatus. The biological signal receiving system has a wireless equipment. The information is transmitted to the biological signal acquisition apparatus. The information corresponds to an operating condition of at least one of an imaging system and the biological signal receiving system. The imaging system acquires ultrasonic image data by transmitting and receiving an ultrasonic wave to and from the object.

Further, according to another embodiment, a method for controlling an ultrasonic diagnostic apparatus includes: controlling a biological signal receiving system to wirelessly transmit a transmission request of a biological signal of an object, receive the biological signal of the object wirelessly transmitted as a response to the transmission request, and output the received biological signal to an output unit; and receiving information wirelessly from the biological signal acquisition apparatus and controlling at least one of an imaging system and the biological signal receiving system according to the information. The transmission request is transmitted to a biological signal acquisition apparatus. The biological signal receiving system has a wireless equipment. The information indicates an operating condition of the biological signal acquisition apparatus. The imaging system acquires ultrasonic image data by transmitting and receiving an ultrasonic wave to and from the object.

An ultrasonic diagnostic apparatus, a biological signal acquisition apparatus and a method for controlling an ultrasonic diagnostic apparatus according to embodiments of the present invention will be described with reference to the accompanying drawings.

FIG. 1 is a functional block diagram of an ultrasonic diagnostic apparatus according to an embodiment of the present invention.

An ultrasonic diagnostic apparatus 1 includes an imaging system 2, an ECG signal receiving system 3, an ECG device control system 4, an apparatus control system 5, an input device 6, and a display unit 7.

On the other hand, wireless ECG devices 8 are attached with an object to be a target of an examination by the ultrasonic diagnostic apparatus 1. The wireless ECG devices 8 may be elements of the ultrasonic diagnostic apparatus 1 or devices independent from the ultrasonic diagnostic apparatus 1. Typically, the two wireless ECG devices 8 are attached.

Each wireless ECG device 8 acquires an ECG signal of an object and outputs the acquired ECG signal wirelessly. For that purpose, each wireless ECG device 8 has an electrode 9 for acquiring an ECG waveform from a body surface of an object, an amplifier 10 for amplifying an ECG signal, and a wireless equipment 11.

From a typical wireless ECG device 8, an ECG signal is output as a digital signal. In a digital type ECG device, the electrode 9 to acquire an ECG waveform is connected with the amplifier 10 and an A/D (analog to digital) converter 12 is connected with the output side of the amplifier 10, as illustrated. Then, an ECG waveform transmitted through the electrode 9 from a body surface of an object is amplified by the amplifier 10, and subsequently, the amplified ECG waveform is converted into a digital signal from an analog signal in the A/D converter 12. The ECG signals converted into the digital signal can be transmitted by the wireless equipment 11.

Furthermore, each wireless ECG device 8 has a wireless ECG monitoring part 13 and a wireless ECG control part 14. The wireless ECG monitoring part 13 has a function to monitor conditions, such as a remaining battery level and a switching state of ON/OFF of a power supply, of the wireless ECG device 8. The wireless ECG monitoring part 13 also has a function to transmit the information, which indicates the conditions of the wireless ECG device 8, obtained as a monitoring result, to the ultrasonic diagnostic apparatus 1 through the wireless equipment 11. On the other hand, the wireless ECG control part 14 has a function to acquire direction information of the wireless ECG device 8 which is wirelessly transmitted from the ultrasonic diagnostic apparatus 1 via the wireless equipment 11, and to control the operations of the wireless ECG device 8 according to the acquired direction information. In the wireless ECG control part 14, the operations of the wireless ECG device 8 such as switching the power supply, the operation clock, acquiring an ECG signal and stopping acquiring an ECG signal can be controlled.

The imaging system 2 of the ultrasonic diagnostic apparatus 1 is a system which acquires ultrasonic image data by transmitting and receiving an ultrasonic wave to and from an object. For that purpose, the imaging system 2 is configured by an apparatus main unit 15 to which an ultrasonic probe 16 is attached. The ultrasonic probe 16 has arrayed ultrasonic transducers. The apparatus main unit 15 has a control part 17 for transmitting and receiving electric signals to and from the respective ultrasonic transducers to generate ultrasonic diagnosis image data based on reception signals received by the respective ultrasonic transducers.

Each of the input device 6 and the display unit 7 is connected with the apparatus main unit 15. Thus, control information such as scanning conditions can be input into the control part 17 from the input device 6 while ultrasonic diagnosis image data acquired by a scan can be displayed on the display unit 7.

The ECG signal receiving system 3 has a function to wirelessly transmit a request for sending an ECG signal of an object, to each wireless ECG device 8, to receive an ECG signal of an object, which has been transmitted wirelessly as a response to the request for sending the ECG signal, and to output an ECG signal to an output device. For that purpose, the ECG signal receiving system 3 has an ECG waveform acquisition part 18 and a wireless equipment 19 for wireless communications with each wireless ECG device 8.

The ECG waveform acquisition part 18 has a function to transmit a request for sending an ECG signal, a sampling rate of an ECG signal which should be transmitted and a request for stopping a transmission of an ECG signal, through the wireless equipment 19 according to an instruction from the input device 6 or the apparatus control system 5, and also a function to acquire the transmitted ECG signals and output them to an output device. The output device for an ECG waveform may be common to the display unit 7 for ultrasonic diagnosis images as illustrated, or may be a dedicated output device for displaying an ECG waveform.

Moreover, the ECG signals acquired in the ECG waveform acquisition part 18 can be used for signal processing to generate ultrasonic diagnosis image data, as needed. Therefore, the ECG waveform acquisition part 18 is configured to be able to output waveform information of ECG signals to the control part 17.

In addition, the ECG signal receiving system 3 has a function to transmit a switching instruction of ON/OFF of the power supply of each wireless ECG device 8, through the wireless equipment 19, according to direction information input from the input device 6.

The ECG device control system 4 has a function to automatically transmit direction information, according to an operating state of at least one of the imaging system 2 and the ECG signal receiving system 3, to the wireless ECG devices 8 wirelessly. Examples of operating states of the imaging system 2 and the ECG signal receiving system 3 include a time when an ultrasonic wave was transmitted by the imaging system 2, a time when an ultrasonic wave was received by the imaging system 2, a time when a request for sending an ECG signal was transmitted to an ECG device from the ECG signal receiving system 3, parameters set for the imaging system 2, an operation mode of the imaging system 2, information specifying applications activated to control the imaging system 2, an operating state of the computer which composes the imaging system 2, attribute information on an object to be imaged by the imaging system 2, a frame rate of ultrasound image data acquired by the imaging system 2, the time set in the imaging system 2 and the like. Therefore, the ECG device control system 4 can transmit direction information, according to at least one of these operating states, to the wireless ECG devices 8.

The times when an ultrasonic wave was transmitted and received by the imaging system 2 are the times when the ultrasonic wave was transmitted and received acoustically. Moreover, examples of an operating state of the computer which composes the imaging system 2 include whether the computer is freezing or not, shutting down or not, sleeping or not and the like. The time set in the imaging system 2 is the internal time of the ultrasonic diagnostic apparatus 1.

In order to have the function mentioned above, the ECG device control system 4 has an apparatus condition monitoring part 20 and an ECG direction part 21.

The apparatus condition monitoring part 20 has a function to create information which indicates an operating state of the ultrasonic diagnostic apparatus 1 by monitoring operating states of the imaging system 2 and the ECG signal receiving system 3 as mentioned above. An ultrasonic image analysis part 20A can be provided in the apparatus condition monitoring part 20. The ultrasonic image analysis part 20A has a function to judge whether ultrasonic diagnosis images are being displayed on the display unit 7 or not, and also a function to acquire display conditions, such as a frame rate, of ultrasonic diagnosis images being displayed, by analyzing ultrasonic diagnosis image data which are an output target to the display unit 7. Thereby, the apparatus condition monitoring part 20 can acquire information with regard to ultrasonic diagnosis images being displayed, as information which indicates an operating state of the ultrasonic diagnostic apparatus 1.

The ECG direction part 21 has a function to wirelessly transmit predetermined direction information according to the information, which indicates an operating state of the ultrasonic diagnostic apparatus 1, created in the apparatus condition monitoring part 20, to the wireless ECG devices 8. That is, the ECG direction part 21 is configured to be able to give the wireless ECG devices 8 instructions depending on a monitoring result, of apparatus conditions of the ultrasonic diagnostic apparatus 1, in the apparatus condition monitoring part 20.

The wireless transmission of direction information to each wireless ECG device 8 can be performed using the wireless equipment 19 for receiving the ECG signals as illustrated in FIG. 1. However, a dedicated wireless device may be provided in order to transmit direction information to the wireless ECG devices 8.

The instruction contents, to the wireless ECG devices 8, corresponding to each operating state of the ultrasonic diagnostic apparatus 1 can be determined arbitrarily by entering the necessary information from the input device 6 into the ECG direction part 21 preliminarily.

For example, it can be determined so that direction information to stop acquiring and transmitting ECG signals in the wireless ECG devices 8 is transmitted from the ECG direction part 21 to the wireless ECG devices 8 in predetermined cases where it is judged that acquisition of the ECG signals is not necessary, such as a case that the computer which composes the imaging system 2 of the ultrasonic diagnostic apparatus 1 is freezing, a case that ultrasonic diagnosis images of an object are not being displayed on the display unit 7, a case that the operation mode of the imaging system 2 is not the display mode of ultrasonic diagnosis images, a case that ultrasonic diagnosis images in the past are being displayed on the display unit 7, a case that applications that are not used during imaging are running and the like. Conversely, it can be also determined so that direction information which starts acquiring and transmitting ECG signals in the wireless ECG devices 8 is transmitted from the ECG direction part 21 to the wireless ECG devices 8 in predetermined cases where it is judged that the ECG signals needs to be acquired, such as a case that an operation mode of the imaging system 2 has become an acquisition mode of ultrasonic diagnosis image data such as color Doppler mode. That is, as direction information corresponding to an operating state of the ultrasonic diagnostic apparatus 1, receiving timing of ECG signals can be transmitted automatically to the wireless ECG devices 8 from the ECG direction part 21, without an operation of the input device 6.

As another example, the electric power supply of each wireless ECG device 8 can be made to be switched to OFF, working with the shutdown of the computer which composes the imaging system 2. That is, the switching directions of the respective electric power supplies of the wireless ECG devices 8 can be transmitted to the wireless ECG devices 8 from the ECG direction part 21 as direction information corresponding to an operating state of the ultrasonic diagnostic apparatus 1.

As a further example, direction information to change an updating rate of ECG signals may also be transmitted to the wireless ECG devices 8 from the ECG direction part 21, according to an operating state of the ultrasonic diagnostic apparatus 1. When each of the wireless ECG devices 8 is a digital type, a controlling value of a sample rate can be transmitted to each wireless ECG device 8 as direction information corresponding to an operating state of the ultrasonic diagnostic apparatus 1.

For example, a controlling value of a sample rate or an instruction for changing the controlling value can be transmitted to each wireless ECG device 8 from the ECG direction part 21 as direction information according to displayed ultrasonic image data. As a case where a controlling value of a sample rate of an ECG signal should be adjusted, a case where a frame rate of displayed ultrasonic diagnosis images is smaller than the sample rate of the ECG signal is mentioned. In such a case, direction information to lower a controlling value of a sample rate of an ECG signal according to a frame rate of displayed ultrasonic diagnosis images can be transmitted to each wireless ECG device 8 from the ECG direction part 21. Thereby, the unnecessary battery consumption in each wireless ECG device 8 can be prevented.

Similarly, in the cases where an operation mode of the imaging system 2 which does not require a high frame rate has been chosen and where an application which does not require a high frame rate has been activated, the unnecessary battery consumption in each wireless ECG device 8 can be prevented by transmitting direction information, to lower a controlling value of a sample rate of an ECG signal, to each wireless ECG device 8 from the ECG direction part 21.

On the contrary, in a case where a high precision ECG waveform is required, such as two dimensional tracking (2DT), three dimensional tracking (3DT), a stress echo examination or the like, direction information to increase an updating rate of an ECG signal in each wireless ECG device 8 can be transmitted to each wireless ECG device 8 from the ECG direction part 21. Thereby, an accuracy in ECG waveform can be improved. The judgment whether an examination requires an improvement of an accuracy in ECG waveform or not can be performed automatically by the ECG direction part 21, based on the selection information of an operation mode of the imaging system 2 and/or the selection information or activation information of applications, which are acquired in the apparatus condition monitoring part 20.

In addition to above, a repetition frequency of an ECG signal transmitted from each wireless ECG device 8 can also be varied according to an acoustic repetition frequency of ultrasonic waves transmitted and received in the imaging system 2. As a result, unnecessary data does not need to be transmitted to the ultrasonic diagnostic apparatus 1 from each wireless ECG device 8 side, and then, the battery consumption in each wireless ECG device 8 can be reduced. Note that, a repetition frequency of ultrasonic waves transmitted and received to and from an object can be acquired, as an imaging parameter from the control part 17 of the imaging system 2, by the apparatus condition monitoring part 20. Similarly, the apparatus condition monitoring part 20 can acquire arbitrary imaging parameters and the ECG direction part 21 can transmit direction information according to the imaging parameters to each wireless ECG device 8.

The apparatus control system 5 has a function to receive the information, which indicates an operating state of the wireless ECG device 8, transmitted wirelessly from the wireless ECG monitoring part 13 of each wireless ECG device 8 and a function to control at least one of the imaging system 2 and the ECG signal receiving system 3 according to the information which indicates operating states of the wireless ECG devices 8. Examples of information, which indicates an operating state of the wireless ECG device 8, transmitted from the wireless ECG monitoring part 13 include the remaining battery level of the wireless ECG device 8, switching information on ON/OFF of the electric power supply of the wireless ECG device 8, and the like.

Note that, the apparatus control system 5 may make the request for sending necessary information to each wireless ECG monitoring part 13 through the wireless equipment 19 so that the apparatus control system 5 can acquire the information, which shows an operating state of the wireless ECG device 8, transmitted from each wireless ECG monitoring part 13 as a response to the request for sending the necessary information.

For the wireless communication between the apparatus control system 5 and each wireless ECG monitoring part 13, the wireless equipment 19 to receive the ECG signals can be used as illustrated in FIG. 1. However, a dedicated wireless equipment may be provided to communicate with the wireless ECG monitoring parts 13.

Examples of a control by the apparatus control system 5 include a control of the ECG signal receiving system 3 for displaying the remaining battery levels of the wireless ECG devices 8, acquired from the wireless ECG monitoring parts 13, on the display unit 7 with ECG waveforms. That is, information, which indicates operating states of the wireless ECG devices 8, acquired from the wireless ECG monitoring parts 13 can be displayed on the display unit 7. Further, the ECG signal receiving system 3 can also be controlled to lower an updating rate of an ECG signal in the wireless ECG device 8 when the remaining battery level of the wireless ECG device 8 is determined to be low by a threshold determination. That is, the transmitting timing of the request for sending an ECG signal, transmitted to each wireless ECG device 8 from the ECG signal receiving system 3 can be controlled according to information which indicates operating states of the wireless ECG devices 8.

Note that, the control of the ECG signal receiving system 3 by the apparatus control system 5 according to operating states of the wireless ECG devices 8 is substantially equivalent to the operation of the ECG direction part 21 according to operating states of the wireless ECG devices 8. Therefore, the controls of the wireless ECG devices 8 according to operating states of the wireless ECG devices 8 may be performed by the ECG direction part 21. In that case, pieces of information which indicate operating states of the wireless ECG devices 8 transmitted from the wireless ECG monitoring parts 13 are given to the ECG direction part 21.

Moreover, the apparatus control system 5 has a time setting part 5A. The time setting part 5A has a function to accord a time, when an ultrasonic wave was received by the imaging system 2, with a time of an ECG signal acquired in the ECG signal receiving system 3. For that purpose, the time setting part 5A is configured to acquire time information for time synchronization.

The time when an ultrasonic wave was received can be acquired, as time information incidental to an ultrasonic reception signal, from the control part 17 of the imaging system 2. Therefore, a time incidental to an ultrasonic reception signal is a time given according to a time set in the control part 17 of the imaging system 2.

On the other hand, the time of an ECG signal can be acquired as time information incidental to the ECG signal acquired in the ECG waveform acquisition part 18. Therefore, the time incidental to an ECG signal is given according to a time set in each wireless ECG device 8.

The time set in the imaging system 2 does not necessarily agree with the time set in each wireless ECG device 8. Accordingly, the time setting part 5A is configured to correct one or both of the time of an ECG signal and the time of an ultrasonic received signal, based on a difference between an internal time of the ultrasonic diagnostic apparatus 1 and each of internal times of the wireless ECG devices 8, acquired from the wireless ECG devices 8.

Thereby, an ECG signal and an ultrasonic reception signal which can be considered to be acquired at a same time can be related with each other. Note that, the time setting part 5A may relate an ECG signal with an ultrasonic reception signal whose time corresponds to that of the ECG signal, instead of the correction of the time information itself.

When a size of data to be a target of the time adjustment is large, a memory required according to the data size is provided with the time matching part 5A. Then, an ECG signal after the time adjustment is given from the time setting part 5A to the ECG waveform acquisition part 18. On the other hand, an ultrasonic reception signal after the time adjustment is given from the time setting part 5A to the control part 17 of the imaging system 2. This makes it possible to display an ECG signal and an ultrasonic reception signal, which can be considered to be acquired at a same time, at same timing. Further, signal processing using an ECG signal and an ultrasonic reception signal whose times have been corrected can be performed.

Note that, a time when an ultrasonic wave was transmitted may be used for the time adjustment instead of a time when an ultrasonic wave was received. That is, display timing of ultrasonic image data and an ECG signal can be adjusted according to a time when an ultrasonic wave was transmitted or received by the imaging system 2 and a time when an ECG signal was received by the ECG signal receiving system 3.

Moreover, a time adjustment instructions to adjust the internal times of the wireless ECG devices 8 to the internal time of the ultrasonic diagnostic apparatus 1 may be transmitted to the wireless ECG devices 8 from the ECG direction part 21, instead of the time adjustment processing in the time setting part 5A. In that case, the internal time of the ultrasonic diagnostic apparatus 1 can be notified to the ECG direction part 21 from the apparatus condition monitoring part 20.

Among the elements which compose the ultrasonic diagnostic apparatus 1 mentioned above, elements for processing of digital information can be configured by installing a control program of the ultrasonic diagnostic apparatus 1 to a computer. However, circuits may be used for configuring those elements.

Next, an operation and an action of the ultrasonic diagnostic apparatus 1 will be described.

Figure 2:
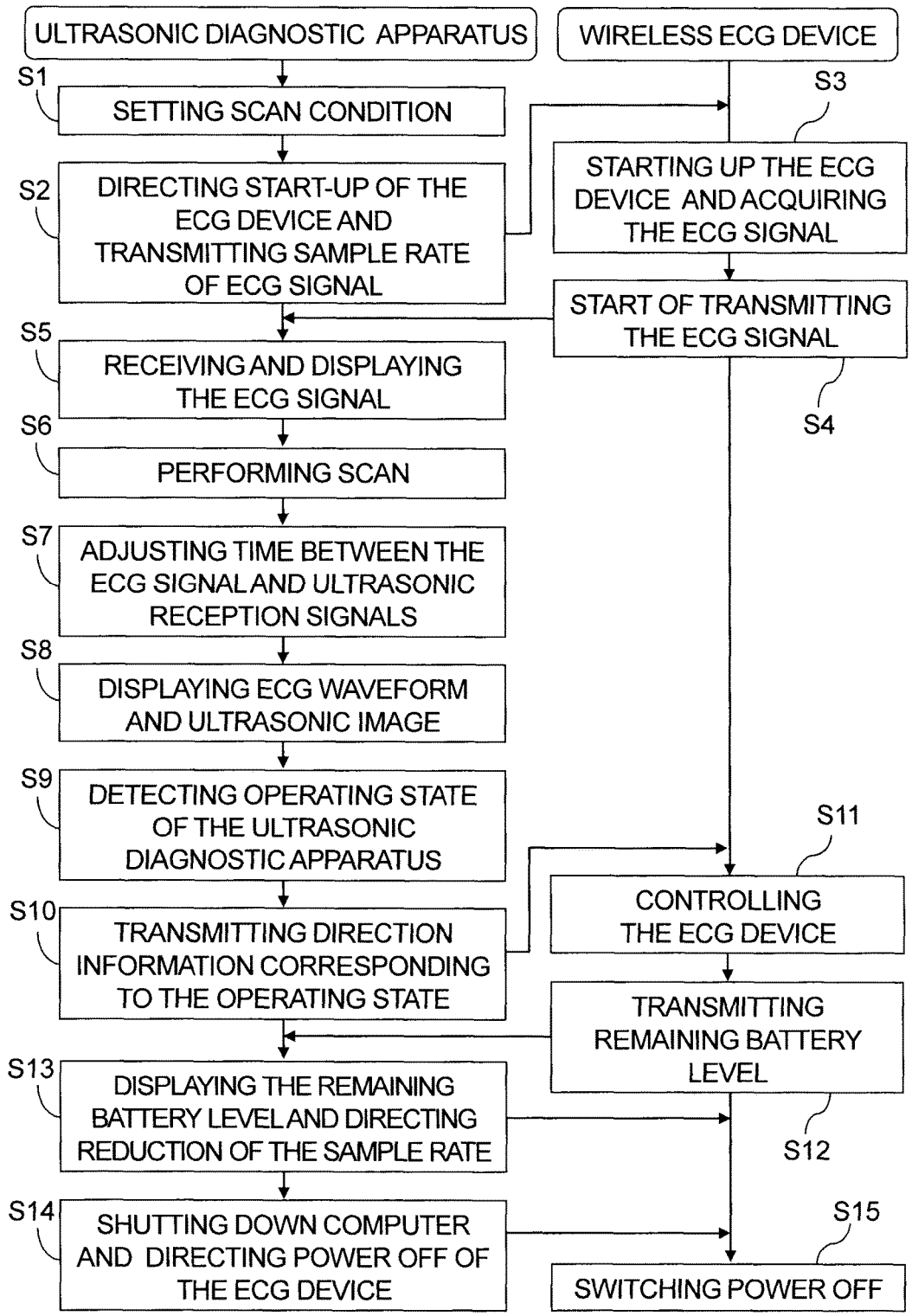
FIG. 2 is a flow chart showing an example flow of imaging with monitoring an ECG waveform of an object by the ultrasonic diagnostic apparatus shown in FIG. 1.

FIG. 2 is a flow chart showing an example flow of imaging with monitoring an ECG waveform of an object by the ultrasonic diagnostic apparatus 1 shown in FIG. 1.

First, the multiple wireless ECG devices 8 are attached to predetermined positions of an object in advance. At this time, the standby power to perform wireless communication in each wireless ECG device 8 is made to the ON state. On the other hand, the computer system which composes the ultrasonic diagnostic apparatus 1 is started up.

Next, in the Step S1, necessary scanning conditions are entered, by the operation of the input device 6, into the control part 17 which controls the imaging system 2 of the ultrasonic diagnostic apparatus 1.

Next, in the Step S2, the start-up instructions of the wireless ECG devices 8 and a sample rate of ECG signals which should be transmitted are entered into the ECG signal receiving system 3 from the input device 6. For this reason, the ECG signal receiving system 3 transmits the sample rate of the ECG signals and the switching instructions to switch the electric power supplies of the wireless ECG devices 8 to the ON state, to the wireless ECG devices 8 through the wireless equipment 19.

Next, in the Step S3, the wireless ECG control part 14 of each wireless ECG device 8 receives the switching instruction of the electric power supply of the wireless ECG device 8 and the sample rate of the ECG signal through the wireless equipment 11. For this reason, the wireless ECG control part 14 switches the electric power supply of the wireless ECG device 8 to the ON state and sets up the designated sample rate. Thereby, an ECG signal is sequentially acquired from the object's body surface by the electrode 9. The acquired ECG signal is amplified by the amplifier 10, and subsequently converted to a digital signal from the analog signal sequentially in the A/D converter 12 according to the sample rate.

Next, in the Step S4, the ECG signal converted into the digital signal is transmitted by the wireless equipment 11. After that, in the Step S5, the ECG signals are received by the wireless equipment 19 of the ultrasonic diagnostic apparatus 1. The received ECG signals are acquired in the ECG waveform acquisition part 18. Then, the ECG waveform acquisition part 18 generates image information showing a waveform of ECG signal and output the image information to the display unit 7. As a result, the object's ECG waveform is displayed on the display unit 7.

For this reason, in the Step S6, a user can perform an ultrasonic scan with referring to the ECG waveform. That is, the imaging system 2 is driven under a control by the control part 17, and ultrasonic wave signals are transmitted towards the object from multiple ultrasonic transducers included in the ultrasonic probe 16. Then, ultrasonic reflection signals reflected inside the object are received by the ultrasonic transducers. The ultrasonic reflection signals received by the ultrasonic transducers are output to the control part 17 as ultrasonic reception signals consisting of electric signals.

Next, in the Step S7, the time setting part 5A performs the time adjustment between the ECG signals and the ultrasonic reception signals, based on the time information incidental to the ECG signals and receipt times of the ultrasonic reception signals in the control part 17. As a result, the ECG signals and the ultrasonic reception signals which can be regarded to have been acquired at a same time can be related with each other.

Next, in the Step S8, ultrasonic diagnosis image data are produced by predetermined signal processing of the ultrasonic reception signals in the control part 17. Then, the produced ultrasonic image data are displayed on the display unit 7 together with the ECG signal after the time adjusting processing. Thereby, a user can observe the ultrasonic images with referring to the ECG waveform which has been acquired at suitable timing.

On the other hand, in the Step S9, operating states of the ultrasonic diagnostic apparatus 1 are monitored by the apparatus condition monitoring part 20. When a preset operating state has been detected, the information which indicates the operating state of the ultrasonic diagnostic apparatus 1 is given to the ECG direction part 21 from the apparatus condition monitoring part 20.

For example, when the computer which composes the ultrasonic diagnostic apparatus 1 has frozen, the freeze of the computer is detected by the apparatus condition monitoring part 20. Alternatively, when the display of ultrasonic diagnosis images on the display unit 7 has been halted, it is detected by the ultrasonic image analysis part 20A that ultrasonic diagnosis images are not being displayed on the display unit 7.

Conversely, when ultrasonic diagnosis images to be displayed with a high frame rate have been displayed on the display unit 7, a kind of the ultrasonic diagnosis images is detected by the ultrasonic image analysis part 20A. Alternatively, an operation mode of the imaging system 2 which should display the ultrasonic diagnosis images with a high frame rate on the display unit 7 is detected by the apparatus condition monitoring part 20.

Next, in the Step S10, the ECG direction part 21 transmits direction information on the wireless ECG devices 8 corresponding to an operating state of the ultrasonic diagnostic apparatus 1, acquired from the apparatus condition monitoring part 20, through the wireless equipment 19. Therefore, in the Step S11, the wireless ECG control part 14 of each wireless ECG device 8 acquires the direction information on the wireless ECG device 8 through the wireless equipment 11. Then, the operation of each wireless ECG device 8 is controlled according to the direction information. For example, when the computer which composes the ultrasonic diagnostic apparatus 1 has frozen, the drives of the wireless ECG devices 8 are stopped. Alternatively, when ultrasonic diagnosis images to be displayed with a high frame rate are displayed, the operation clock of each wireless ECG device 8 is set to a higher value.

Such a detection of an operating state of the ultrasonic diagnostic apparatus 1 and a control of the wireless ECG devices 8 corresponding to the operating state are performed repeatedly, as necessary.

Moreover, information which indicates a device status of each wireless ECG device 8 can be transmitted to the ultrasonic diagnostic apparatus 1 from each wireless ECG device 8 at a desired timing. For example, when a remaining battery level of wireless ECG device 8 has become not more than a predetermined value, the remaining battery level can be informed to the ultrasonic diagnostic apparatus 1, as a device status of the wireless ECG device 8.

In that case, in the Step S12, it is detected by the wireless ECG monitoring part 13 that a remaining battery level of wireless ECG device 8 has become not more than a predetermined value. Then, the wireless ECG monitoring part 13 transmits the information, which indicates the remaining battery level of the wireless ECG device 8, through the wireless equipment 11.

Next, in the Step S13, the apparatus control system 5 acquires the information, which indicates the remaining battery level of the wireless ECG device 8, through the wireless equipment 19. Then, the ECG signal receiving system 3 is controlled to display the remaining battery level of the wireless ECG device 8, on the display unit 7, together with an ECG waveform. Thereby, the ECG waveform acquisition part 18 displays the remaining battery level of the wireless ECG device 8 on the display unit 7 together with the ECG waveform. For this reason, a user can check the remaining battery level of the wireless ECG device 8.

Furthermore, the apparatus control system 5 can instruct lowering a sample rate of the ECG signal by controlling the ECG signal receiving system 3. That is, an instruction value of the sample rate of the ECG signal corresponding to the remaining battery level of the wireless ECG device 8 is given to the ECG waveform acquisition part 18 from the apparatus control system 5. Therefore, a new sample rate of the ECG signal to be transmitted is transmitted from the ECG waveform acquisition part 18 through the wireless equipment 19.

Then, the wireless ECG control part 14 of the wireless ECG device 8 acquires the instruction value of the sample rate through the wireless equipment 11. Then, the wireless ECG control part 14 controls the wireless ECG device 8 so that the sample rate of the ECG signal becomes the instruction value. As a result, the operation clock of the wireless ECG device 8 is reduced and a battery drain can be delayed.

Furthermore, when the computer which composes the control part 17 of the ultrasonic diagnostic apparatus 1 is shut down after completing an ultrasonic scan, each wireless ECG device 8 can be made to be the sleep state, along with the shutdown.

In that case, in the Step S14, the control part 17 is shut down according to the instructions from the input device 6. Then, the apparatus condition monitoring part 20 detects the input of the shutdown instruction to the computer, which composes the control part 17, or the shutdown of the computer and gives a detection result to the ECG direction part 21. Therefore, the ECG direction part 21 transmits the OFF instructions of the electric power supplies to the wireless ECG devices 8 through the wireless equipment 19.

Then, in the Step S15, the wireless ECG control part 14 of each wireless ECG device 8 receives the OFF instruction of the electric power supply through the wireless equipment 11. Subsequently, the wireless ECG control part 14 switches the electric power supply of the wireless ECG device 8 to the OFF state. As a result, each wireless ECG device 8 becomes the sleep state along with the shutdown of the ultrasonic diagnostic apparatus 1.

Note that, the OFF instruction of the electric power supply to the wireless ECG device 8 is preferred to be transmitted only when the electric power supply of the wireless ECG device 8 is in the ON state. Accordingly, the wireless ECG monitoring part 13 may transmit the information, which indicates that the electric power supply of the wireless ECG device 8 has been switched to the ON state, to the ultrasonic diagnostic apparatus 1. Thus, the ECG direction part 21 can transmit the OFF instruction of the electric power supply to the wireless ECG device 8 only when the electric power supply of the wireless ECG device 8 is in the ON state.

That is, the ultrasonic diagnostic apparatus 1 as described above is an apparatus configured to perform bothway communications with the wireless ECG devices 8 so that one can be controlled according to information transmitted from the other.

Therefore, the wireless ECG devices 8 having no cable can be easily attached and detached to an object, by the ultrasonic diagnostic apparatus 1. That is, complicated work regarding cables required for connecting wired ECG apparatuses can be avoided. For this reason, the ultrasonic diagnostic apparatus 1 is effective especially when an ECG sensor part must be attached to an object promptly, like a stress echo examination.

In addition, a delay of an ECG signal, which may arise due to connecting the wireless ECG device 8 with the ultrasonic diagnostic apparatus 1, can be resolved by the time adjusting function between the ECG signal and an ultrasonic reception signal. For this reason, an ECG waveform can be displayed with ultrasonic diagnosis images at suitable timing.

Furthermore, the ultrasonic diagnostic apparatus 1 can automatically control the electric power supply and the operation clock of each wireless ECG device 8 according to operating states of the ultrasonic diagnostic apparatus 1.

Therefore, a battery drain, which is a problem in case of using the wireless ECG device 8, can be minimized.

That is, practical realization of the wireless ECG device 8 can be attained by the ultrasonic diagnostic apparatus 1, by resolving the problems which may arise due to a use of the wireless ECG device 8.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

For example, a biological signal, such as a PCG (phonocardiogram) signal, a respiration signal or a sphygmogram signal, which have periodicity may be acquired in addition to an ECG signal or instead of an ECG signal. In that case, at least one biological signal acquisition apparatus which wirelessly outputs a biological signal is attached to an object.

Then, a biological signal receiving system which acquires a biological signal, a biological signal acquisition apparatus control system which controls the biological signal acquisition apparatus according to an apparatus state of the ultrasonic diagnostic apparatus 1 and an apparatus control system which controls the ultrasonic diagnostic apparatus 1 according to the information from the biological signal acquisition apparatus can be provided in the ultrasonic diagnostic apparatus 1, similarly to the case where an ECG signal is acquired.

For example, by installing a control program for the ultrasonic diagnostic apparatus 1 to the computer included in the ultrasonic diagnostic apparatus 1 having the wireless equipment 19, the computer included in the ultrasonic diagnostic apparatus 1 can function as the biological signal receiving system, the biological signal acquisition apparatus control system and the apparatus control system.

Figure 3:
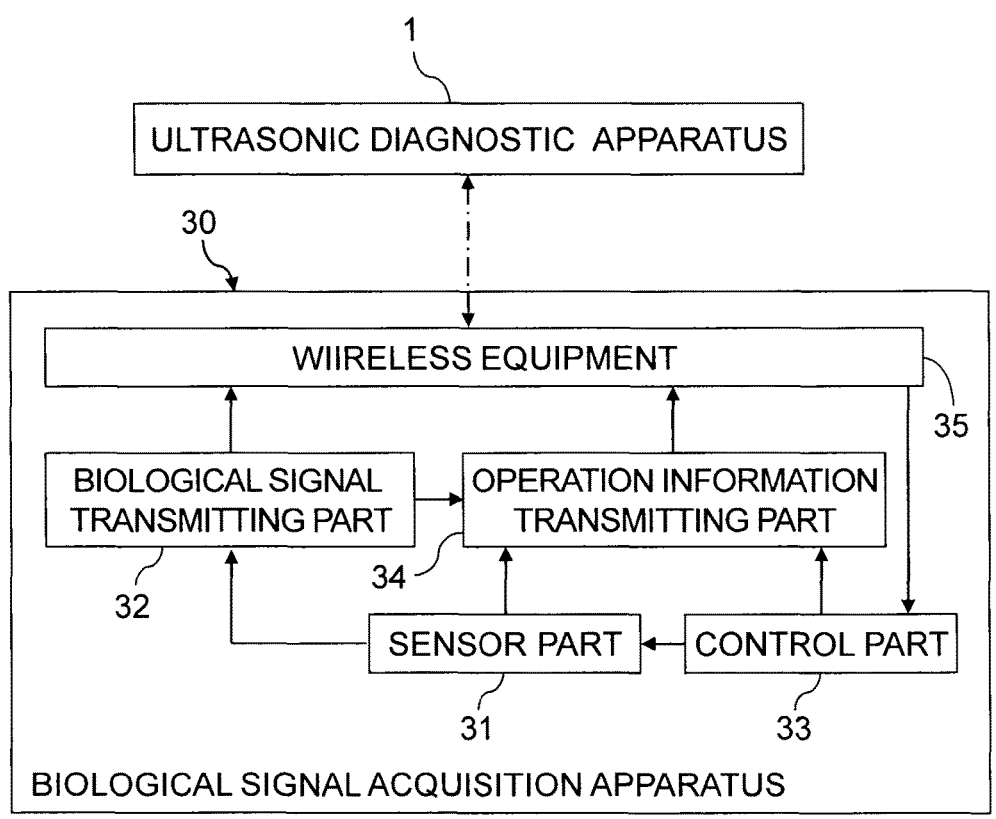
FIG. 3 is a configuration diagram of a typical biological signal acquisition apparatus.

FIG. 3 is a configuration diagram of a typical biological signal acquisition apparatus.

A biological signal acquisition apparatus 30 can be configured using a sensor part 31, a biological signal transmitting part 32, a control part 33, an operation information transmitting part 34, and a wireless equipment 35. Note that, illustration of an amplifier, an A/D converter and the like is omitted.

The sensor part 31 is a component to acquire a biological signal from an object. In the case of the wireless ECG device 8 shown in FIG. 1, the sensor part 31 is composed of the electrode 9, the generation circuit of an operation clock signal attached to the electrode 9, the electric power supply and so on.

The biological signal transmitting part 32 is a component which has a function to wirelessly receive the request for sending a biological signal, from the ultrasonic diagnostic apparatus 1, and to wirelessly transmit the biological signal to the ultrasonic diagnostic apparatus 1 as a response to the request for sending the biological signal. In each wireless ECG device 8 shown in FIG. 1, the wireless equipment 11 which operates autonomously has a function as the biological signal transmitting part 32. Of course, the biological signal transmitting part 32 which controls the wireless equipment 11 may be provided to each wireless ECG device 8 shown in FIG. 1.

The control part 33 is a component which has a function to wirelessly receive information according to an operating state of the ultrasonic diagnostic apparatus 1, from the ultrasonic diagnostic apparatus 1, and to control the sensor part 31 according to the received information. In the example of the wireless ECG device 8 shown in FIG. 1, the wireless ECG control part 14 functions as the control part 33. Note that, the control of the sensor part 31 includes switching the electric power supply, the control of the operation clock, start of acquiring an ECG signal, stop of acquiring an ECG signal and the like.

The operational information transmitting part 34 is a component which has a function to transmit information, showing an operating state of at least one of the sensor part 31, the biological signal transmitting part 32 and the control part 33, to the ultrasonic diagnostic apparatus 1. In the example of the wireless ECG device 8 shown in FIG. 1, the wireless ECG monitoring part 13 functions as the operational information transmitting part 34.

Each of the biological signal transmitting part 32, control part 33, and the operational information transmitting part 34, mentioned above, are configured to be able to communicate with the ultrasonic diagnostic apparatus 1, using the wireless equipment 35. The independent wireless equipment 35 may be connected to each of the biological signal transmitting part 32, control part 33, and the operational information transmitting part 34. In that case, the wireless equipment 35 may also be a component of each of the biological signal transmitting part 32, control part 33, and the operational information transmitting part 34.

Then, the controls of the ultrasonic diagnostic apparatus 1 and the biological signal acquisition apparatus 30 can be performed similarly to those in the embodiment explained with referring to FIG. 1 and FIG. 2.

For example, the ultrasonic diagnostic apparatus 1 can be controlled by a control method having: a step of controlling a biological signal receiving system, having the wireless equipment 19, to wirelessly transmit a transmission request of a biological signal of an object to the biological signal acquisition apparatus 30, receive the biological signal of the object wirelessly transmitted as a response to the transmission request, and output the received biological signal to an output unit such as the display unit 7; and a step of wirelessly transmitting information corresponding to operating conditions of at least one of the imaging system 2, which acquires ultrasonic image data by transmitting and receiving an ultrasonic wave to and from the object, and the biological signal receiving system, to the biological signal acquisition apparatus 30, using the wireless equipment 19.

Alternatively, the ultrasonic diagnostic apparatus 1 can be also controlled by a control method having: a step of controlling a biological signal receiving system, having the wireless equipment 19, to wirelessly transmit a transmission request of a biological signal of an object to the biological signal acquisition apparatus 30, receive the biological signal of the object wirelessly transmitted as a response to the transmission request, and output the received biological signal to an output unit such as the display unit 7; and a step of receiving information, which indicates operating conditions of the biological signal acquisition apparatus 30, wirelessly from the biological signal acquisition apparatus 30 and controlling at least one of the imaging system 2, which acquires ultrasonic image data by transmitting and receiving an ultrasonic wave to and from the object, and the biological signal receiving system, according to the information which indicates the operating conditions of the biological signal acquisition apparatus 30.

As a more specific example, when the operational information transmitting part 34 of the biological signal acquisition apparatus 30 is configured to transmit the remaining battery level of the control part 33 to the ultrasonic diagnostic apparatus 1, the apparatus control system 5 of the ultrasonic diagnostic apparatus 1 can display the remaining battery level on an output device to output a biological signal or another output device in the case where the apparatus control system 5 has received the remaining battery level of the biological signal acquisition apparatus 30. In addition, the reduction of a sample rate of a biological signal can be directed by the apparatus control system 5.

Note that, one of the ultrasonic diagnostic apparatus 1 and the biological signal acquisition apparatus 30 may be configured to wirelessly transmit control signals as direction information to the other so that the other can operate according to the control signals. Alternatively, one of the ultrasonic diagnostic apparatus 1 and the biological signal acquisition apparatus 30 may be configured to wirelessly transmit information, which indicates operating states and the like, to the other so that the other can operate according to control signals generated based on the received information. That is, control signals of the ultrasonic diagnostic apparatus 1 and the biological signal acquisition apparatus 30 may be generated in any of the ultrasonic diagnostic apparatus 1 and the biological signal acquisition apparatus 30.

What is claimed is:

1. An ultrasonic diagnostic apparatus comprising:
    an imaging system, having an ultrasonic probe, configured to acquire ultrasonic image data by transmitting and receiving an ultrasonic wave to and from an object;
    a biological signal receiving system, having circuitry and a wireless equipment, configured to wirelessly transmit a transmission request of a biological signal of the object, receive the biological signal of the object wirelessly transmitted as a response to the transmission request, and output the received biological signal to a display, the transmission request being transmitted to a biological signal sensor; and
    biological signal sensor control circuitry configured to wirelessly transmit a control value of a sample rate in the biological signal sensor to the biological signal sensor, the control value of the sample rate corresponding to a frame rate of ultrasonic image data which are being displayed.

2. An ultrasonic diagnostic apparatus of claim 1, wherein said biological signal sensor control circuitry is configured to transmit information to the biological signal sensor, the information corresponding to
    at least one of a time when an ultrasonic wave has been transmitted by said imaging system,
    a time when an ultrasonic wave has been received by said imaging system,
    a time when the transmission request of the biological signal has been transmitted from said biological signal receiving system to the biological signal sensor,
    a parameter set for said imaging system,
    an operation mode of said imaging system,
    information specifying an application activated for controlling said imaging system, an operating condition of a computer composing said imaging system,
    attribute information of the object imaged by said imaging system,
    a frame rate of the ultrasonic image data acquired by said imaging system, and
    a time set in said imaging system.

3. An ultrasonic diagnostic apparatus of claim 1, wherein said biological signal sensor control circuitry is configured to transmit a receiving timing of the biological signal at the biological signal sensor.

4. An ultrasonic diagnostic apparatus of claim 1, wherein said biological signal sensor control circuitry is configured to transmit a switching instruction of a power supply of the biological signal sensor, to the biological signal sensor.

5. An ultrasonic diagnostic apparatus comprising:
    an imaging system, having an ultrasonic probe, configured to acquire ultrasonic image data by transmitting and receiving an ultrasonic wave to and from an object;
    a biological signal receiving system, having circuitry and a wireless equipment, configured to wirelessly transmit a transmission request of a biological signal of the object, receive the biological signal of the object wirelessly transmitted as a response to the transmission request, and output the received biological signal to a display, the transmission request being transmitted to a biological signal sensor;
    an apparatus control circuitry configured to wirelessly receive information from the biological signal sensor and control said imaging system according to the information, the information indicating an operating condition of the biological signal sensor; and
    a biological signal sensor control circuitry configured to wirelessly transmit a control value of a sample rate in the biological signal sensor, to the biological signal sensor, the control value of the sample rate corresponding to a frame rate of ultrasonic image data which are being displayed.

6. An ultrasonic diagnostic apparatus of claim 5, wherein said apparatus control circuitry is configured to control a transmission timing of the transmission request of the biological signal, according to the information indicating the operating condition, the transmission request being transmitted from said biological signal receiving system to the biological signal sensor.

7. An ultrasonic diagnostic apparatus of claim 5, wherein said apparatus control circuitry is configured to adjust each display timing of the ultrasonic image data and the biological signal according to
    a time at which an ultrasonic wave has been transmitted or received by said imaging system, and
    a time at which the biological signal has been received by said biological signal receiving system.

8. An ultrasonic diagnostic apparatus of claim 5, wherein said apparatus control circuitry is configured to display a remaining battery level of the biological signal sensor on the display or another display when the remaining battery level has been received.

9. A control method for an ultrasonic diagnostic apparatus comprising:
    controlling a biological signal receiving system to wirelessly transmit a transmission request of a biological signal of an object, receive the biological signal of the object wirelessly transmitted as a response to the transmission request, and output the received biological signal to a display, the transmission request being transmitted to a biological signal sensor, the biological signal receiving system having circuitry and a wireless equipment; and
    transmitting a control value of a sample rate in the biological signal sensor, wirelessly using the wireless equipment, from said ultrasonic diagnostic apparatus to the biological signal sensor, the control value of the sample rate corresponding to a frame rate of ultrasonic image data which are being displayed.

10. A control method for an ultrasonic diagnostic apparatus comprising:

controlling a biological signal receiving system to wirelessly transmit a transmission request of a biological signal of an object, receive the biological signal of the object wirelessly transmitted as a response to the transmission request, and output the received biological signal to a display, the transmission request being transmitted to a biological signal sensor, the biological signal receiving system having a wireless equipment;

receiving information wirelessly from the biological signal sensor and controlling an imaging system according to the information, the information indicating an operating condition of the biological signal sensor, the imaging system acquiring ultrasonic image data by transmitting and receiving an ultrasonic wave to and from the object; and transmitting a control value of a sample rate in the biological signal sensor, wirelessly using the wireless equipment, from said ultrasonic diagnostic apparatus to the biological signal sensor, the control value of the sample rate corresponding to a frame rate of ultrasonic image data which are being displayed.

* * * * *